(12) United States Patent
Hao et al.

(10) Patent No.: US 8,999,506 B2
(45) Date of Patent: Apr. 7, 2015

(54) METHOD OF ONE-POT SYNTHESIS OF WATER-SOLUBLE NANOPARTICLES EXHIBITING UP-CONVERSION LUMINESCENCE

(75) Inventors: Jianhua Hao, Hong Kong (CN); Zhen-Ling Wang, Hong Kong (CN); Songjun Zeng, Hong Kong (CN); Helen L. W. Chan, Hong Kong (CN)

(73) Assignee: The Hong Kong Polytechnic University, Hong Kong (CN)

( * ) Notice: Subject to any disclaimer, the term of this patent is extended or adjusted under 35 U.S.C. 154(b) by 0 days.

(21) Appl. No.: 13/425,946

(22) Filed: Mar. 21, 2012

(65) Prior Publication Data
US 2013/0251995 A1   Sep. 26, 2013

(51) Int. Cl.
*C09K 11/00* (2006.01)
*B32B 5/16* (2006.01)
*C09K 11/77* (2006.01)

(52) U.S. Cl.
CPC .............. *B32B 5/16* (2013.01); *C09K 11/7773* (2013.01); *G01N 2458/40* (2013.01); *Y10T 428/2982* (2013.01)

(58) Field of Classification Search
USPC ........... 423/263, 21.1; 428/402; 252/301.4 H, 252/582; 250/458.1, 459.1
See application file for complete search history.

(56) References Cited

U.S. PATENT DOCUMENTS 7,651,771 B2 *   1/2010   Meyer et al. ................. 428/403
8,389,958 B2 *   3/2013   Vo-Dinh et al. ............ 250/459.1
2009/0042314 A1   2/2009   Capobianco et al.

FOREIGN PATENT DOCUMENTS

WO   2008/048190   *   4/2008

OTHER PUBLICATIONS

Gai, S. et al., "Synthesis of Magnetic, Up-Conversion Luminescent, and Mesoporous Core-Shell-Structured Nanocomposites as Drug Carriers", *Adv. Funct. Matter*, 20, (2010), pp. 1166-1172.
Vetrone, F. et al., "Intracellular imaging of HeLa cells by non-functionalized $NaYF_4$: $Er^{3+}$, $Yb^{3+}$ upconverting nanoparticles", *Nanoscale*, 2, (2010), pp. 495-498.
Wang, F. et al., "Simultaneous phase and size control of upconversion nanocrystals through lanthanide doping", *Nature*, vol. 463 (Feb. 25, 2010), pp. 1061-1065.
Wang, Z. et al., "Simultaneous synthesis and functionalization of water-soluble up-conversion nanoparticles for in-vitro cell and nude mouse imaging", *Nanoscale*, 3, (2011), pp. 2175-2181.
Xu, C. et al., "Upconversion luminescence and magnetic properties of ligand-free monodisperse lanthanide doped $BaGdF_5$ nanocrystals", *J. of Luminescence*, 131, (2011), pp. 2544-2549.

* cited by examiner

*Primary Examiner* — Steven Bos
(74) *Attorney, Agent, or Firm* — Leydig, Voit & Mayer, Ltd.

(57) ABSTRACT

The present invention relates to a method for synthesizing water-soluble particles, the method includes providing a solution including a lanthanide compound, a halide compound, and a first solvent; introducing a capping agent into the solution to form a mixture; heating the mixture under pressure to produce the particles; and recovering the particles from the mixture. The present invention also relates to a water-soluble particle having a surface functional group. The particles exhibit up-conversion luminescence utilizing NIR excitation, wherein the particles are synthesized in a one-pot process.

25 Claims, 18 Drawing Sheets

METHOD OF ONE-POT SYNTHESIS OF WATER-SOLUBLE NANOPARTICLES EXHIBITING UP-CONVERSION LUMINESCENCE

FIELD OF THE INVENTION

The invention relates to water-soluble nanoparticles exhibiting up-conversion luminescence. The invention also relates to a method of one-pot synthesis of the particles.

BACKGROUND OF THE INVENTION

Fluorescent labelling techniques have been widely used in pharmacological and biological researches as well as clinical diagnosis. Current commercial fluorescent labelling agents includes organic dye, fluorescent proteins, noble-metal nanoparticles and quantum dots (QDs) as biological luminescent probes encounter several challenges. Organic dyes, such as fluorescein, rhodamine, dansyl chloride, are the most conventional and widely used commercial fluorescent labelling agents. They have high quantum efficiency, but the rapid photo bleaching limits the available detection duration. In addition, the short fluorescent lifetimes and broad spectral features do not help in reducing the background interference and increase the signal to noise ratio. Compared with traditional organic dyes, fluorescent proteins developed by cell itself from the expressed genes have improved resistance to photo-bleaching. Fluorescent proteins have been commercialized and promptly occupied the market. However, the variety of fluorescent proteins is limited, and the generic expression of a fluorescent protein in the cell requires high levels of skill and funding. Commercial noble-metal nanoparticles such as gold colloid are potentially suitable candidates for biosensors and bio-imaging because they can scatter and absorb visible light. These nanoparticles are biocompatible but their optical properties in the visible region may overlap with natural proteins. QDs have attracted a great deal of attention as bioconjugates for live cell in imaging, labelling and diagnostics. Unfortunately, QDs are still controversial due to their inherent toxicity and blinking effect, although they are endowed with many advantages such as high quantum yields, narrow emission, broad ultraviolet (UV) excitation, etc.

Rare-earth doped phosphors (REPs) have been proposed as a new generation of biological luminescent probes for both optical and magnetic resonance bio-imaging. REPs have attracted much attention in bio-applications due to their attractive chemical and optical features such as superior photo-stability, high emitting light intensity, long fluorescence lifetimes suitable for time-gated detection, low toxicity, and free of the blinking effect as shown in QDs. In particular, multicolor up-conversion luminescence with excitation of NIR can be realized by controlling lanthanide dopant-host combination. The up-conversion techniques utilizing NIR excitation rather than ultra-violet (UV) excitation allow significantly reduction of background auto-fluorescence, photobleaching and photo damage to biological specimens, and therefore improve the signal-to-noise ratio and sensitivity during biological detections. In addition, REPs can be applied in both confocal/multi-photon microscopy and in wholebody optical imaging systems, which is preferable for both in-vitro and in-vivo imaging.

Unfortunately, many REPs synthesized by solution methods such as co-thermolysis in non-hydrolytic solvents or liquid-solid-solution process are unsatisfactory for the use as biolabels because of the low water-solubility and biocompatibility due to the presence of the hydrophobic surface ligands. Some techniques of surface modification have been explored to improve the water-solubility and biocompatibility, including the conversion of hydrophobic REPs into water-soluble by the coating of silica or amphiphilic polymers. Secondly, the existing synthesis and surface modification techniques are usually complex and time-consuming, with the organic wastes resulted from the course of synthesis and subsequent surface treatment pollute the environment. In addition, the synthesis techniques are often limited to small-batch and lab-scale, which significantly restricts the commercial development of the REPs. Thirdly, the stability of the REPs in physiological conditions is generally undesirable and requires further improvements. Hence, it is an object of the present application to introduce a facile and environmental friendly method for the synthesis of biological luminescent probes in which the aforesaid shortcomings are mitigated or at least to provide a useful alternative.

SUMMARY OF THE INVENTION

According to one aspect of the present invention, there is provided a method for synthesizing water-soluble particles, the method comprising the steps of
providing a solution comprising a lanthanide compound, a halide compound and a first solvent; introducing a capping agent to the solution to form a mixture; heating the mixture under pressure to produce a plurality of particles; and recovering the particles from the mixture.

According to another aspect of the present invention, there is provided a water-soluble particle comprising surface functional group, the particles exhibit up-conversion luminescence utilizing NIR excitation, wherein the particles are synthesized by a one-pot process.

BRIEF DESCRIPTION OF THE DRAWINGS

FIG. 1A shows the particles at low-magnification; FIG. 1B shows the particles at high-magnification; FIG. 1C shows the particles at high-resolution; and FIG. 1D shows the selected area electron diffraction (SAED) pattern of the particles.

FIG. 4A shows the particles at low-magnification; FIG. 4B shows the particles at high-magnification; FIG. 4C shows the selected area electron diffraction (SAED) pattern of the particles; and FIG. 4D shows the particles at high-resolution.

FIG. 7B shows the XRD patterns of the particles modified by 3MA; FIG. 7C shows the XRD patterns of the particles modified by 6AA; FIG. 7D shows the XRD patterns of the particles modified by PEG; and FIG. 7A shows the XRD patterns of the standard $NaYF_4$ powders.

FIG. 8A shows the FTIR spectra of the particles modified by 3MA and the corresponding spectra of 3MA; FIG. 8B shows the FTIR spectra of the particles modified by 6AA and the corresponding spectra of 6AA; and FIG. 8C shows the FTIR spectra of the particles modified by PEG and the corresponding spectra of PEG.

FIG. 9A shows the particle colloidal without excitation of 975 nm laser; and FIG. 9B shows the particle colloidal with excitation of 975 nm laser.

FIG. 10A shows the up-conversion luminescence spectra of the particles modified by 3MA; FIG. 10B shows the up-conversion luminescence spectra of the particles modified by 6AA; FIG. 10C shows the up-conversion luminescence spectra of the particles modified by PEG.

FIG. 13A shows an image of the particles modified by 3MA; FIG. 13B shows an image of the particles modified by 6AA; and FIG. 13C shows an image of the particles modified by PEG. ($A_o$), ($B_o$) and ($C_o$) are the corresponding bright field images of HeLa cells. The overlay of the corresponding fluorescent microscopy images and bright field images are shown in ($A_1$), ($B_1$) and ($C_1$), respectively.

FIG. 14A shows an image of the particles modified by 3MA; FIG. 14B shows an image of the particles modified by 6AA; and FIG. 14C shows an image of the particles modified by PEG. ($A_o$), ($B_o$) and ($C_o$) are the corresponding bright field images of A549 cells. The overlay of the corresponding fluorescent microscopy images and bright field images are shown in ($A_1$), ($B_1$) and ($C_1$), respectively.

FIG. 16A shows an image of the particles modified by 3MA; FIG. 16B shows an image of the particles modified by 6AA; and FIG. 16C shows an image of the particles modified by PEG. ($A_o$), ($B_o$) and ($C_o$) are the corresponding bright field images of HeLa cells. The overlay of the corresponding fluorescent microscopy images and bright field images are shown in ($A_1$), ($B_1$) and ($C_1$), respectively.

DESCRIPTION OF THE PREFERRED EMBODIMENTS

Figure 1:
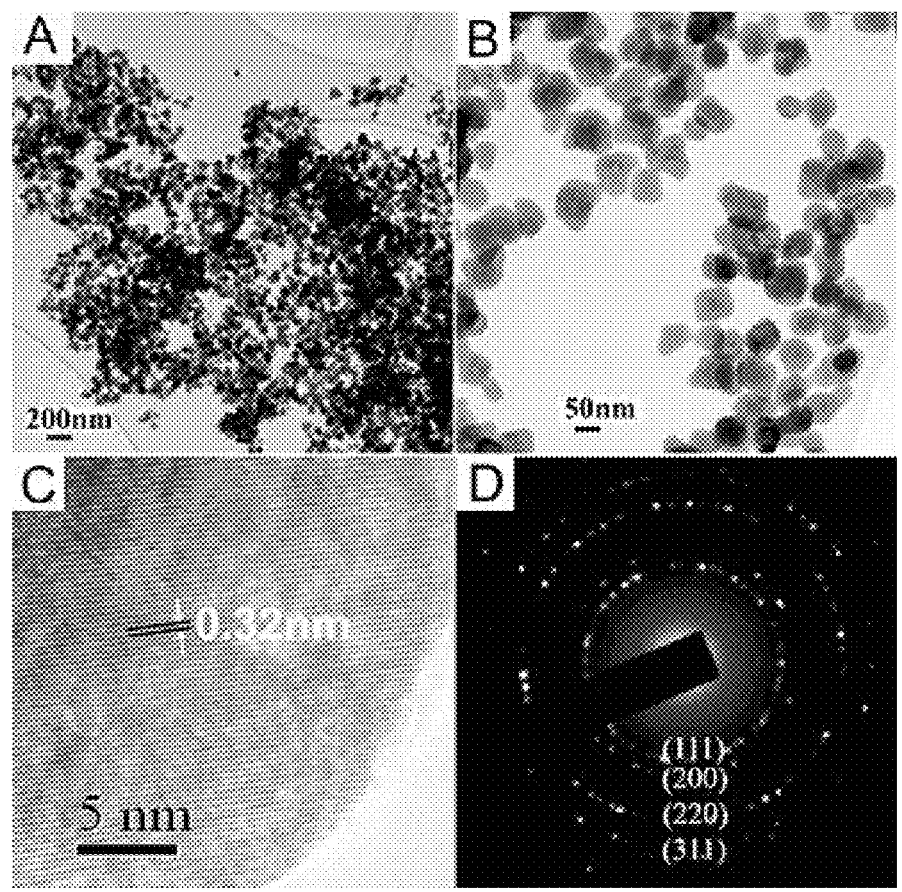
FIG. 1 shows Transmission Electron Micrograph (TEM) of a plurality of $NaYF_4:Yb^{3+}/Er^{3+}$ particles modified by 3-mercaptopropionic acid (3MA) as embodied in the present invention.

In an aspect of the present invention, it is provided a method of synthesizing water-soluble particles as up-conversion phosphors for fluorescent labelling. The method involves a one-pot synthesis technique which is facile and environmental friendly. Specifically, the method comprising the steps of providing a solution comprising a lanthanide compound, a halide compound and a first solvent; introducing a capping agent to the solution to form a mixture; heating the mixture under pressure to produce a plurality of particles; and recovering the particles from the mixture. In the following description, a number of embodiments of the method, and the particles as synthesized by the embodied method, including $NaYF_4:Yb^{3+}/Er^{3+}$, $BaGdF_5:Yb^{3+}/Er^{3+}$ are described.

The lanthanide compound as embodied in the present method can be lanthanide trihydrochloride. In one embodiment, the lanthanide trihydrochloride is selected from the group consisting of $YCl_3$, $YbCl_3$ and a mixture thereof, and $NaYF_4:Yb^{3+}/Er^{3+}$ particles are synthesized according to the embodied method. Preferably, the mole ratio of $YbCl_3$ to $YCl_3$ as dissolved in the first solvent is in a range from about 12% to about 20%, and the mole ratio of $ErCl_3$ to $YCl_3$ is in a range from about 1% to about 5%. Concentration of the lanthanide trihydrochloride in the solution is in a range from about 0.025 mmol per ml to about 0.1 mmol per ml. The $NaYF_4:Yb^{3+}/Er^{3+}$ particles produced have sizes in a range from about 50 nm to about 80 nm.

In another embodiment, $BaGdF_5:Yb^{3+}/Er^{3+}$ particles can also be synthesized according to the embodied method. The resulted $BaGdF_5:Yb^{3+}/Er^{3+}$ particles are of the size range from about 8 nm to about 15 nm.

In an embodied method, the first solvent can be ethylene glycol. Alternatively, the first solvent can be water, or a mixture of ethylene glycol and water. In another embodied method, the lanthanide compound is dissolved in the first solvent to form a first solution, and separately the halide compound is dissolved in the first solvent to form a second solution. The solution is then formed by combining the first and the second solutions. Preferably, the first solvent in the first solution comprises ethylene glycol, and the first solvent in the second solution comprises water.

The halide compound can be selected from a group consisting of chloride, fluoride and a mixture thereof. Preferably, the chloride can be selected from a group consisting of NaCl, BaCl$_2$ and a mixture thereof. The chloride can be dissolved in the first solvent at a concentration ranged from about 0.025 mmol per ml to about 0.1 mmol per ml. Alternatively, the fluoride can be selected from a group consisting of NaF, NH$_4$F, NH$_4$HF$_2$ and a mixture thereof. The fluoride can be dissolved in the first solvent at a concentration ranged from about 0.25 mmol per ml to about 1.0 mmol per ml. The capping agent can be selected from a group consisting of 3-mercaptopropionic acid, 6-aminocaproic acid, poly(ethylene glycol) methyl ether (PEG), polyethylenimine (PEI) and a mixture thereof. The capping of the particles introduces surface function group onto the particles, with the surface function group can be selected from —COOH, —NH$_2$, —SH, —OH or a mixture thereof.

The providing step of the embodied method may further include a stirring step. Preferably, the stirring step includes stirring for about 20 min to 60 min. The heating step may involve heating at a temperature ranged from about 120° C. to about 220° C. Preferably, the heating step includes heating for about 4 hrs to about 48 hrs under a pressure ranged from about 1.5 MPa to about 2.5 MPa. More preferably, the heating step is carried out in an autoclave. After the heating step, the embodied method may further include a cooling step. The cooling can be carried out by natural cooling.

The recovering step may further include the step of separating the particles via centrifugation, and collecting the particles. The recovering step may be followed by a washing step, that is, to wash the recovered particles by a second solvent. The second solvent can be ethanol, and the washing step can be repeated for 2 times to 5 times. The washed particles can be subsequently dried in vacuum at a temperature ranged from about 45 to about 70° C. for about 12 hrs to about 24 hrs.

Therefore, the present invention provides a facile, environmental-friendly, and one-pot synthesis technique, through which water-soluble particles or specifically, nanoparticles can be synthesized. The particles can be rare-earth doped phosphors (REPs), or specifically, lanthanide doped phosphors, for the purpose of biological labeling. The solvent being used in the synthesis can be ethylene glycol, which has lower pollution than some of the commonly used organic solvents such as hexadecane, oleylamine and oleic acid, etc. In addition, surface functional groups, such as —COOH, —NH$_2$, and —SH can be directly introduced onto the particle surfaces during the synthesis, without any further surface treatment is required. The surface functional groups allow a significant improve in water-solubility and bio-compatibility. Furthermore, the cost of synthesis of the particles using the present invention is low as lanthanide compound, such as lanthanide trichloride can be used as starting materials. The synthesized particles as embodied in this invention exhibit visible and near-infrared (NIR) emission in various human carcinoma cells lines and nude mouse through up-conversion that is a two- or multi-photon process where the NIR excitation light (typically 980 nm) is up-converted to higher energies from the deep-UV, visible to the NIR, which demonstrate high cell uptake, long lasting localization, and low cytotoxicity in the cells.

In a specific embodiment, water-soluble NaYF$_4$:Yb$^{3+}$/Er$^{3+}$ nanoparticles were prepared by a modified hydrothermal method. Typically, 1 mmol in total of YCl$_3$, YbCl$_3$ and ErCl$_3$ with the molar ratio of 39:10:1, were dissolved in 20 mL of ethylene glycol. Around 10 mL of aqueous solution containing 5 mmol of NaF was added to above solution and stirred for about 30 min. To improve the water-solubility and endow the functionalization of particles, some capping agents including 3-mercaptopropionic acid (3 MA, HSCH$_2$CH$_2$COOH, 99%, Aldrich), 6-aminocaproic acid [6AA, H$_2$N(CH$_2$)$_5$COOH, 99%, Aldrich] and poly(ethylene glycol) methyl ether (PEG, average molecular=5000, Aldrich) were added to the above mixture respectively. The as-obtained mixture was then transferred into a Teflon bottle held in a stainless steel autoclave, which was sealed and hydrothermally treated at 190° C. for 24 hrs. After the autoclave was cooled to room temperature under natural cooling, i.e. cooling under room condition, the precipitates were separated by centrifugation, washed with ethanol for three times, and dried in vacuum at 50° C. for 12 hrs to obtain the as-prepared samples.

Morphology of the particles as synthesized was observed using a transmission electron microscope (TEM, JEOL 2010). Structure of the particles was studied by an Oxford instrument energy dispersive X-ray spectroscopy (EDS) system equipped with the TEM. Phase structure was characterized by a Bruker D8 Advance X-ray diffractometer (XRD) with Cu-Kα radiation (λ=0.15406 nm). Fourier transform infrared (FTIR) spectra were recorded for KBr disks containing powder sample with a MAGNA-IR760 Spectrometer E. S. P. (Nicolet). Up-conversion photoluminescence spectra were recorded using an FLS920P Edinburgh Analytical Instrument apparatus equipped with a diode laser (MDL-975 nm, 2 W) as the excitation source.

Figure 2:
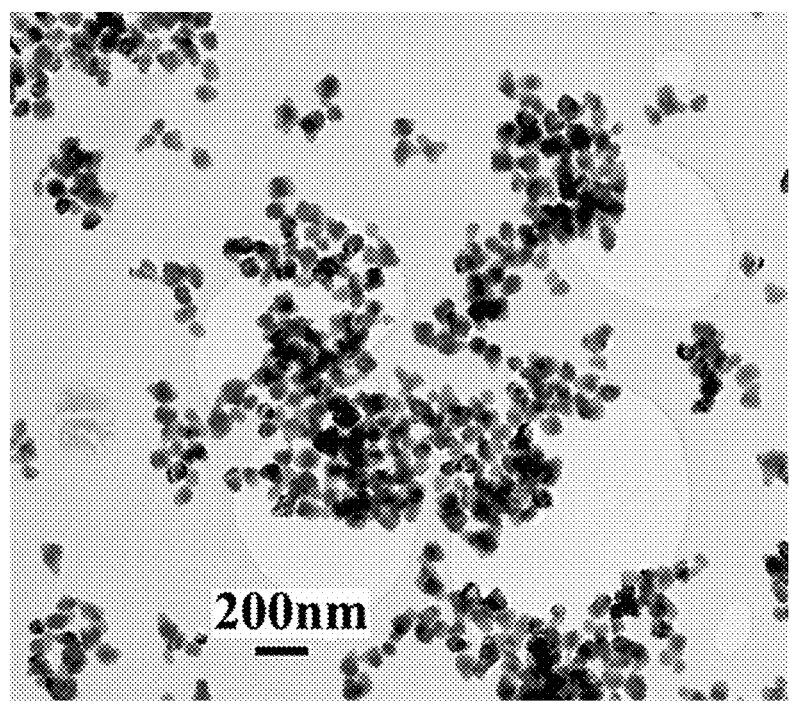
FIG. 2 shows a Transmission Electron Micrograph (TEM) of a plurality of $NaYF_4:Yb^{3+}/Er^{3+}$ particles modified by 6-aminocaproic acid (6AA) as embodied in the present invention at low magnification.
Figure 3:
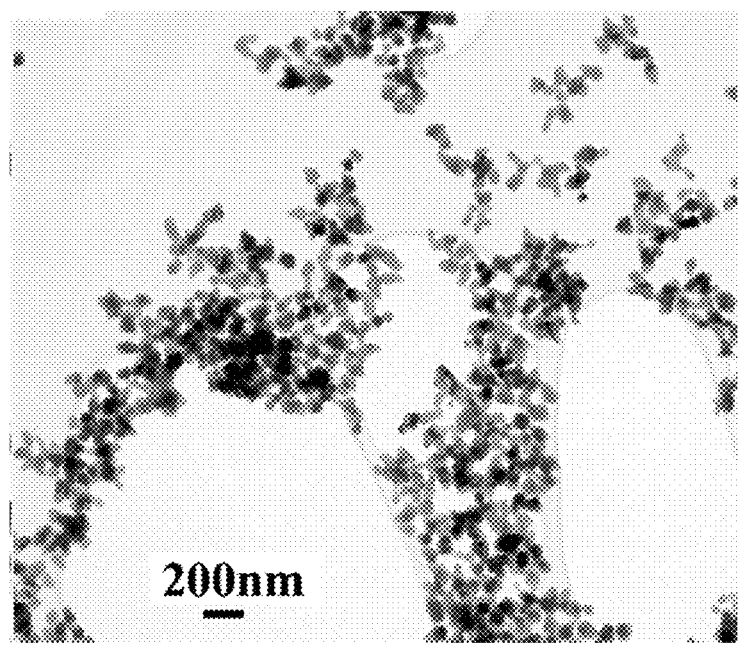
FIG. 3 shows a Transmission Electron Micrograph (TEM) of a plurality of $NaYF_4:Yb^{3+}/Er^{3+}$ particles modified by poly (ethylene glycol) methyl ether (PEG) as embodied in the present invention at low magnification.

A typical TEM image as shown in FIG. 1 reveals that the as-prepared NaYF$_4$:Yb$^{3+}$/Er$^{3+}$ particles modified by 3MA are composed of nanoparticles with an average diameter of about 60 nm, see FIGS. 1A and 1B. The high-magnification TEM image as shown in FIG. 1B reveals the irregular morphology, which may result from the random conglomeration of some primary NaYF$_4$:Yb$^{3+}$, Er$^{3+}$ nanocrystals. High-resolution TEM (HRTEM) can provide atomic resolution. The HRTEM image as shown in FIG. 1C shows lattice fringes with an observed d-spacing of 0.32 nm, which is in good agreement with the lattice spacing in the (111) planes of cubic NaYF$_4$ (0.316 nm). The selected area electron diffraction (SAED) pattern shown in FIG. 1D indicates the cubic structure and polycrystalline characteristic of the particles. The morphology of particles is not affected by substituting 3MA for 6AA or PEG, as shown in FIG. 2 and FIG. 3, respectively.

Figure 4:
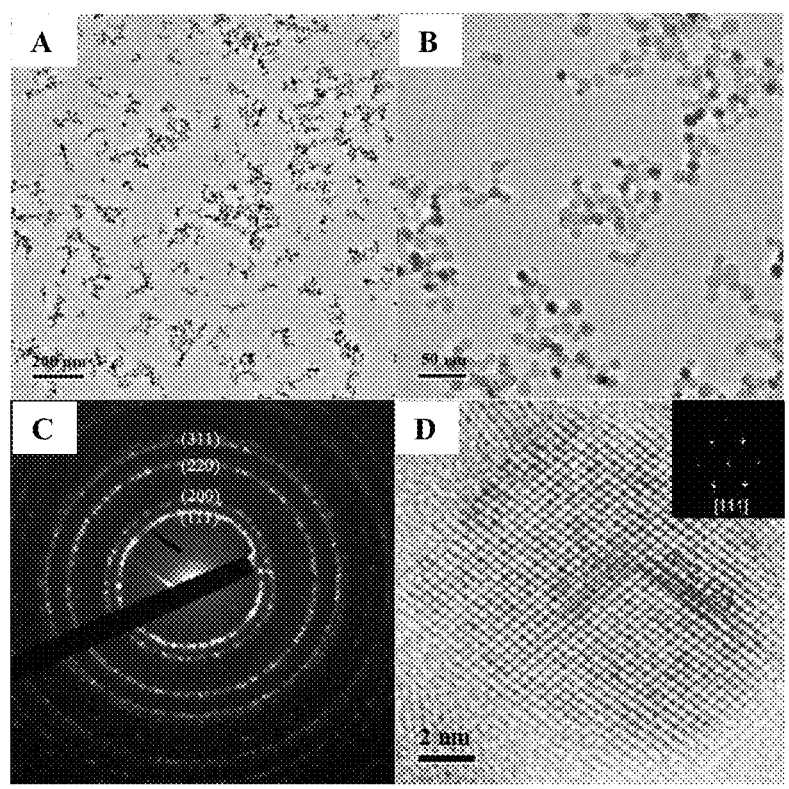
FIG. 4 shows Transmission Electron Micrographs (TEM) of a plurality of $BaGdF_5:Yb^{3+}/Er^{3+}$ particles modified by polyethylenimine (PEI) as embodied in the present invention.
Figure 5:
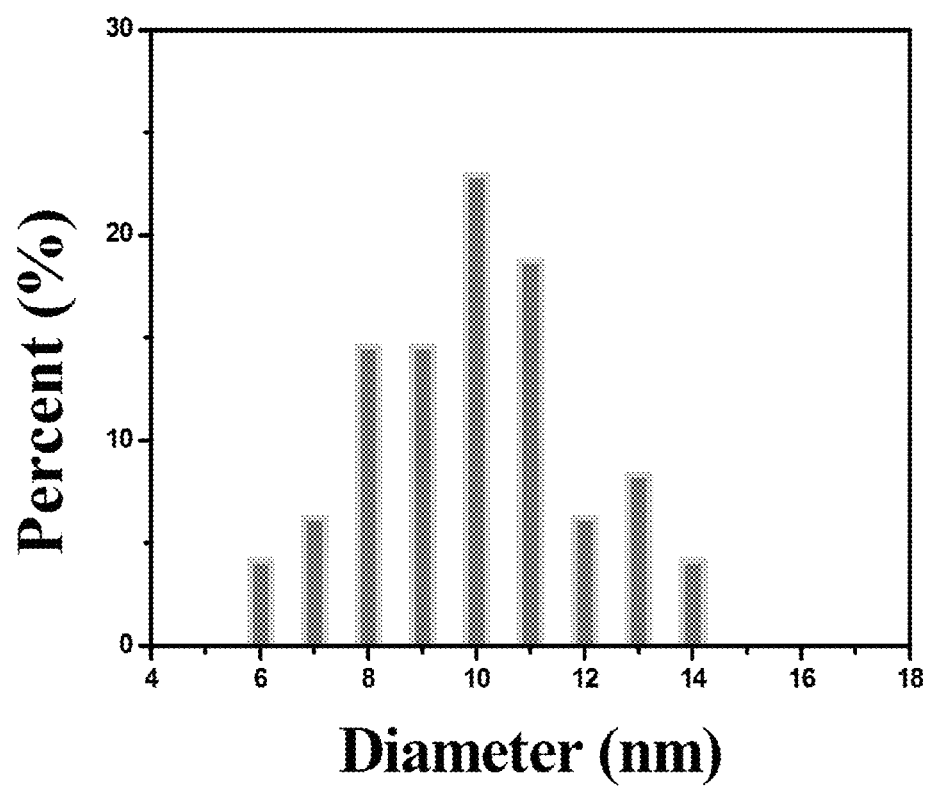
FIG. 5 shows a histogram showing the size distribution of the $BaGdF_5:Yb^{3+}/Er^{3+}$ particles modified by polyethylenimine (PEI) as embodied in the present invention. The histogram shows the particle size distribution with an average size of about 10 nm.

FIG. 4 shows the TEM images of the BaGdF$_5$:Yb$^{3+}$/Er$^{3+}$ particles modified by polyethylenimine (PEI) as synthesized in another embodiment. FIG. 4A and FIG. 4B shows the average diameter of the particles is about 10 nm. FIG. 4C shows the selected area electron diffraction (SAED) pattern of the particles which indicates the cubic structure and polycrystalline characteristic of the particles. FIG. 4D shows the particles under high-resolution TEM. The HRTEM image shows the particle has high crystallinity and the inter-planar distances of HRTEM are determined to be 2.13 Å, matching well with the (2-20) lattice plane of the face-center cubic (FCC) phase of BaGdF$_5$. A histogram showing the size distribution of the BaGdF$_5$:Yb$^{3+}$/Er$^{3+}$ particles modified by polyethylenimine (PEI) is shown in FIG. 5. The histogram shows the particle size distribution with an average size of about 10 nm. It should be denoted that the size distribution of the particles as synthesized by the embodied method seems to be poorer than that by nonhydrolytic solution route, though the satisfactory results for bioimaging of these particles in cell and small animals could be achieved, which will be mentioned in the below sections. The particle size distribution of these particles might be improved through accurately optimizing reaction conditions such as the molar ratio of reactants, pH value, the variety of lanthanide salts and fluorides, the amount of capping agents, reaction time, reaction temperature and so on.

Figure 6:
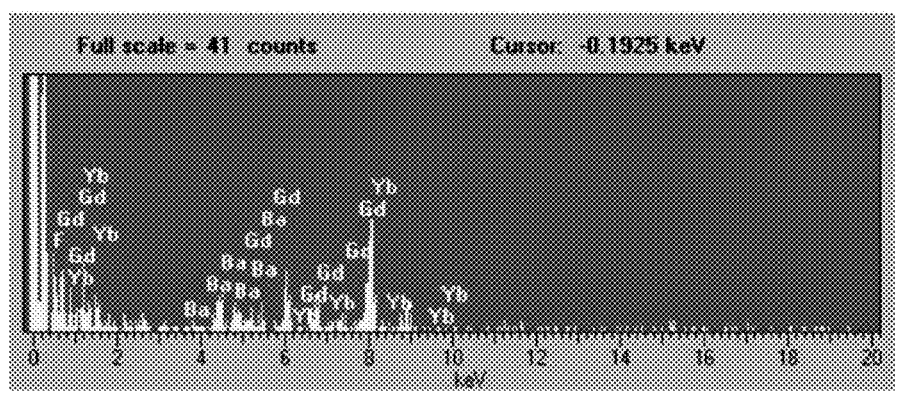
FIG. 6 shows the Energy Dispersive Spectroscopy (EDS) of the $BaGdF_5:Yb^{3+}/Er^{3+}$ particles modified by polyethylenimine (PEI) as embodied in the present invention.

The structure of the as-synthesized BaGdF$_5$:Yb$^{3+}$/Er$^{3+}$ particles are studied by the Energy Dispersive Spectroscopy (EDS) equipped with the TEM. FIG. 6 shows the EDS spectrum of the BaGdF$_5$:Yb$^{3+}$/Er$^{3+}$ particles modified by polyethylenimine (PEI), which reveals that the particles are mainly composed of Ba, Gd, F, and the dopant Yb.

Figure 7:
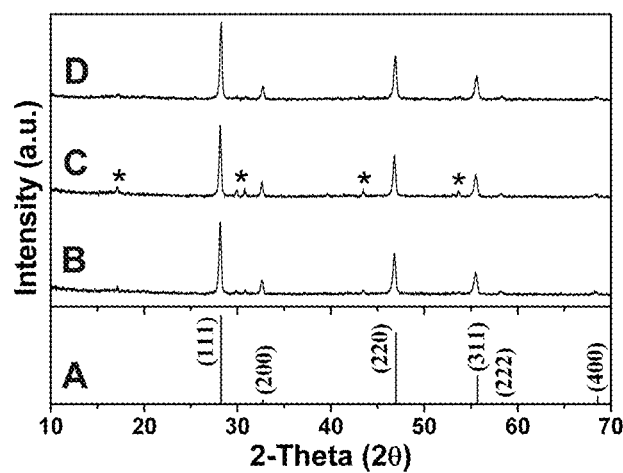
FIG. 7 shows the X-ray Diffraction (XRD) patterns of the $NaYF_4:Yb^{3+}/Er^{3+}$ particles as embodied in the present invention when compared with the standard $NaYF_4$ powders.

FIG. 7 shows the x-ray diffraction (XRD) patterns of the NaYF$_4$:Yb$^{3+}$/Er$^{3+}$ particles modified by 3MA (B), 6AA (C), PEG (D), and standard data of NaYF$_4$ powders (A, JSPDF No. 77-2042), respectively. It can be seen from the XRD results that the phase of the particles as modified by 3MA, 6AA and PEG are mainly in accordance with the face-centered cubic structure of NaYF$_4$ powder. The amount of hexagonal phase is very small for all samples because the peaks (denoted as star marks) attributed to the hexagonal structure of NaYF$_4$ powders (JSPDF No. 16-0334) are very weak.

Figure 8:
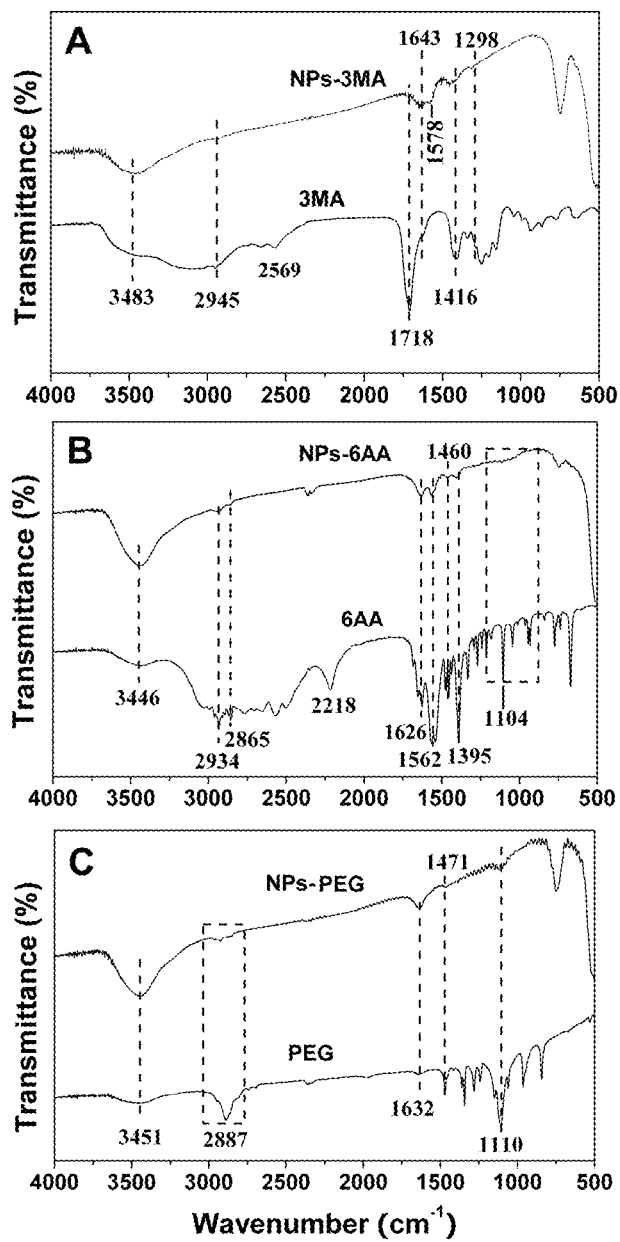
FIG. 8 shows the Fourier Transform Infrared (FTIR) spectra of the surface modified $NaYF_4:Yb^{3+}/Er^{3+}$ particles as embodied in the present invention.

The presence of the functional ligands at the surface of the NaYF$_4$:Yb$^{3+}$/Er$^{3+}$ particles is evident from FTIR spectra as shown in FIG. 8. We compared FTIR spectrum of the particles as modified by 3MA (represented as NPs-3MA in the spectrum) with that of 3MA, as shown in FIG. 8A. The absorption band at ~3483 cm$^{-1}$ is attributed to the stretching vibration of hydroxyl groups, and the difference between them is that the absorption band for 3MA is very broad. The absorption peaks at 2945 cm$^{-1}$ in the two spectra are due to the asymmetrical stretching vibration modes of CH$_2$ group. The absorption band at 2569 cm$^{-1}$ arising from stretching vibration of —SH group is not present in the spectrum of NPs-3MA, which might indicate that the —SH group end of 3MA is bonded on the surface of NaYF$_4$:Yb$^{3+}$/Er$^{3+}$ particles because of the strong binding ability between mercapto group and metal ions. The strong absorption peak at 1718 cm$^{-1}$ for 3MA is due to the asymmetrical stretching vibration modes of C=O group, while the weak peaks at 1643 cm$^{-1}$ and 1578 cm$^{-1}$ for NPs-3MA are resulted from the asymmetrical and symmetrical stretching vibration modes of C=O group. The weak absorption bands at ~1416 and ~1230 cm$^{-1}$ shown in the spectrum of NPs-3MA are corresponding to the in-plane bend vibration of C—OH and stretching vibration of C—O groups of 3MA, respectively. From the above analysis, we could deduce that 3MA is capped on the surface of NaYF$_4$:Yb$^{3+}$/Er$^{3+}$ particles synthesized by the embodied method. FIG. 8B shows the FTIR spectra of 6AA and the particles as modied by 6AA (represented as NPs-6AA in the spectrum) for comparison. It can be seen that a broad absorption band at about 3446 cm$^{-1}$ due to the O—H and/or N—H stretching vibration, the asymmetrical and symmetrical stretching vibration modes of CH$_2$ group at 2934 and 2865 cm$^{-1}$, the asymmetrical and symmetrical stretching vibration modes of C=O group at 1460 and 1395 cm$^{-1}$, the absorption bands at 1626, 1562 cm$^{-1}$ and many weak peaks at around 1104 cm$^{-1}$ due to amine groups vibration, are present at the spectrum of NPs-6AA, which also indicates that 6AA can be efficiently adsorbed on the surface of NaYF$_4$:Yb$^{3+}$/Er$^{3+}$ particles. Similarly, the surface of the NaYF$_4$:Yb$^{3+}$/Er$^{3+}$ particles could be functionalized by PEG, as confirmed by FTIR results. As shown in FIG. 8C, the broad band at 3451 cm$^{-1}$ is indexed to the O—H stretching vibration. The bands at around 2887 cm$^{-1}$ are due to the asymmetrical and symmetrical stretching vibration modes of CH$_2$ group. The absorption bands at 1632, 1471 and around 1110 are attributed to the methylene scissoring and C—O—C stretching vibration.

Figure 9:
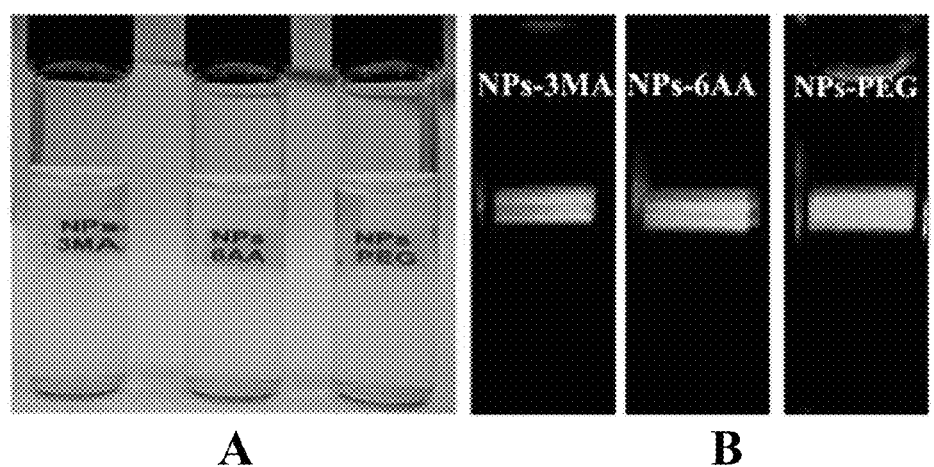
FIG. 9 shows photographs of the 0.05 wt % colloidal solution of the surface modified $NaYF_4:Yb^{3+}/Er^{3+}$ particles as embodied in the present invention.
Figure 10:
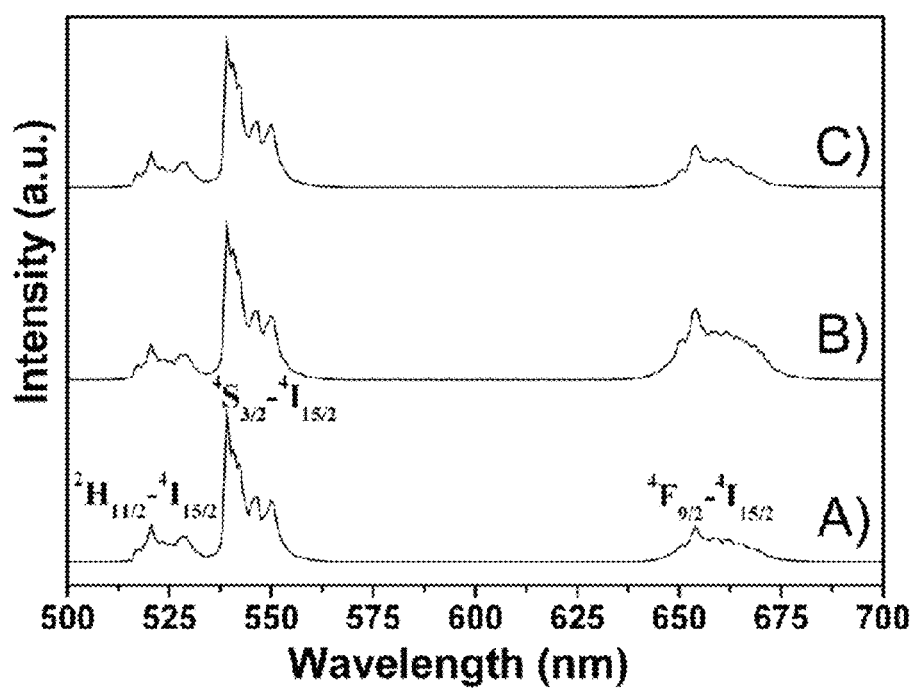
FIG. 10 shows the up-conversion luminescence spectra of 0.05 wt % colloidal solution of the surface modified $NaYF_4:Yb^{3+}/Er^{3+}$ particles as embodied in the present invention.

Modification by 3MA, 6AA and PEG allows the surface of particles be functionalized by —COOH, —NH$_2$, —SH or —OH groups, which could not only improve the water-solubility of particles but also increase the possibility of entering cells' interior. The colloidal dispersions of the NaYF$_4$:Yb$^{3+}$/Er$^{3+}$ particles modified by 3MA, 6AA and PEG as shown in FIG. 9A demonstrate the good water-solubility and optical transparency of these samples. Under excitation with a 975 nm laser, these three dispersions exhibit prominent green emission as shown in FIG. 9B. The up-conversion luminescent spectra for these three samples as shown in FIG. 10, demonstrate similarity in profile and comprise peaks at 514-532 nm, 535-556 nm and 645-675 nm, corresponding to $^2H_{11/2} \rightarrow ^4I_{15/2}$, $^4S_{3/2} \rightarrow ^4I_{15/2}$ and $^4F_{9/2} \rightarrow ^4I_{15/2}$ transitions of doped Er$^{3+}$ ions, respectively. Infrared photons are firstly absorbed by the strong transition from the ground state $^2F_{7/2}$ to the first excited state $^2F_{5/2}$ in the Yb$^{3+}$ ions. In successive steps, energy transfers carry these excitations over to the excited state $^4I_{11/2}$ in an Er$^{3+}$ ion nearby. Electrons in the state $^4I_{11/2}$ of Er$^{3+}$ ion can be further excited to $^4F_{7/2}$ by another Yb$^{3+}$ $^2F_{5/2}$ excitation. Firstly, the excited electrons relax non-radiatively to $^2H_{11/2}$, $^4S_{3/2}$ and $^4F_{9/2}$ energy levels, and then decay further to the ground state of Er$^{3+}$ to emit green and red emission. The presence of some organic groups such as —COOH, —NH$_2$, —SH, and —OH on the particle surface may result in the non-radioactive relaxation across these energy gaps of $^2H_{11/2}-^4F_{9/2}$ and $^4S_{3/2}-^4F_{9/2}$, so the green emission is more prominent than red emission for all samples synthesized in the procedure.

Figure 11:
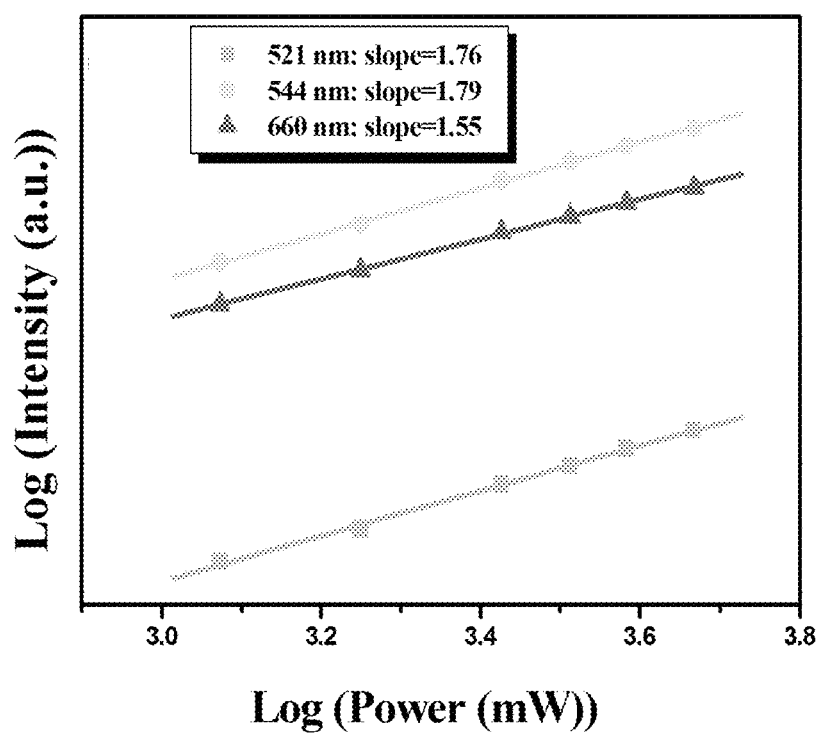
FIG. 11 shows Log-Log plots of the upconversion luminescence intensity versus excitation power for the $BaGdF_5:Yb^{3+}/Er^{3+}$ particles modified by polyethylenimine (PEI) as embodied in the present invention.

FIG. 11 shows the Log-Log plots of the up-conversion luminescence intensity versus excitation power for the BaGdF$_5$:Yb$^{3+}$/Er$^{3+}$ particles modified by polyethylenimine (PEI), as synthesized by the embodied method. The slopes of the linear fits for the green and red emissions at 521, 544 and 660 nm are 1.76, 1.79 and 1.55, respectively, revealing a two photon process is required by both green and red UC emissions.

Figure 12:
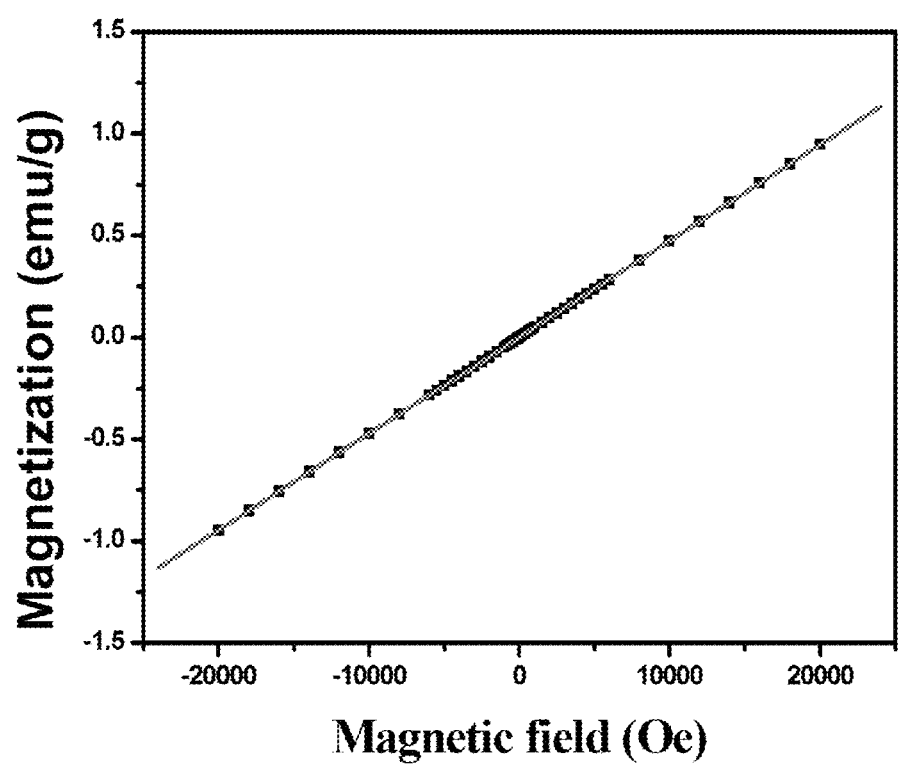
FIG. 12 shows a plot of magnetization versus applied magnetic field for the $BaGdF_5:Yb^{3+}/Er^{3+}$ particles modified by polyethylenimine (PEI) as embodied in the present invention at room temperature.

In addition, it is noted that the BaGdF$_5$:Yb$^{3+}$/Er$^{3+}$ particles as synthesized by the embodied method exhibit multifunctional characteristic such as showing excellent paramagnetism. FIG. 12 shows the magnetization as a function of applied magnetic field of the as-synthesized BaGdF$_5$:Yb$^{3+}$/Er$^{3+}$ particles. The particles show paramagnetism under an applied field ranging from −20 to 20 kOe, unlike the behaviour of Gd atoms which exhibit a ferromagnetic behaviour below 289 K. In general, the magnetic properties of Gd$^{3+}$ arise from seven unpaired inner 4f electrons, which are closely bound to the nucleus and effectively shielded by the outer closed shell electrons 5s$^2$5p$^6$ from the crystal field. The separation between the Gd$^{3+}$ ions in the matrix are too far to render sufficient overlap of the orbitals associated with the partially filled 4f electrons shells of the Gd$^{3+}$ ions, which is necessary for ferromagnetism. The calculated magnetic mass susceptibility of the as-synthesized BaGdF$_5$:Yb$^{3+}$/Er$^{3+}$ particles at room temperature is $4.72 \times 10^{-5}$ emu g$^{-1}$ Oe$^{-1}$. Moreover, the RM magnetization of the BaGdF$_5$:Yb$^{3+}$/Er$^{3+}$ particles at 20 kOe is around 0.95 emu/g. The magnetic mass susceptibility of the BaGdF$_5$:Yb$^{3+}$/Er$^{3+}$ particles is bigger than that of small sized KGdF$_4$ and is close to the reported value of the NaGdF$_4$, GdF$_3$:Eu$^{3+}$ and Gd$_2$O$_3$:Eu$^{3+}$ particles potentially used in common bio-separation technique, which are $7.75 \times 10^{-5}$, $9.4 \times 10^{-5}$ and $1.3 \times 10^{-4}$ emu g$^{-1}$ Oe$^{-1}$, respectively. Compared to other up-conversion nanocrystals such as BaYF$_5$, CaF$_2$, SrF$_2$, BaF$_2$ and LaF$_3$, the paramagnetism of BaGdF$_5$ nanocrystals allow them to be used in more areas. For example, the paramagnetism of BaGdF$_5$ nanocrystals presents potential applications in bioseparation and magnetic resonance imaging (MRI).

Figure 13:
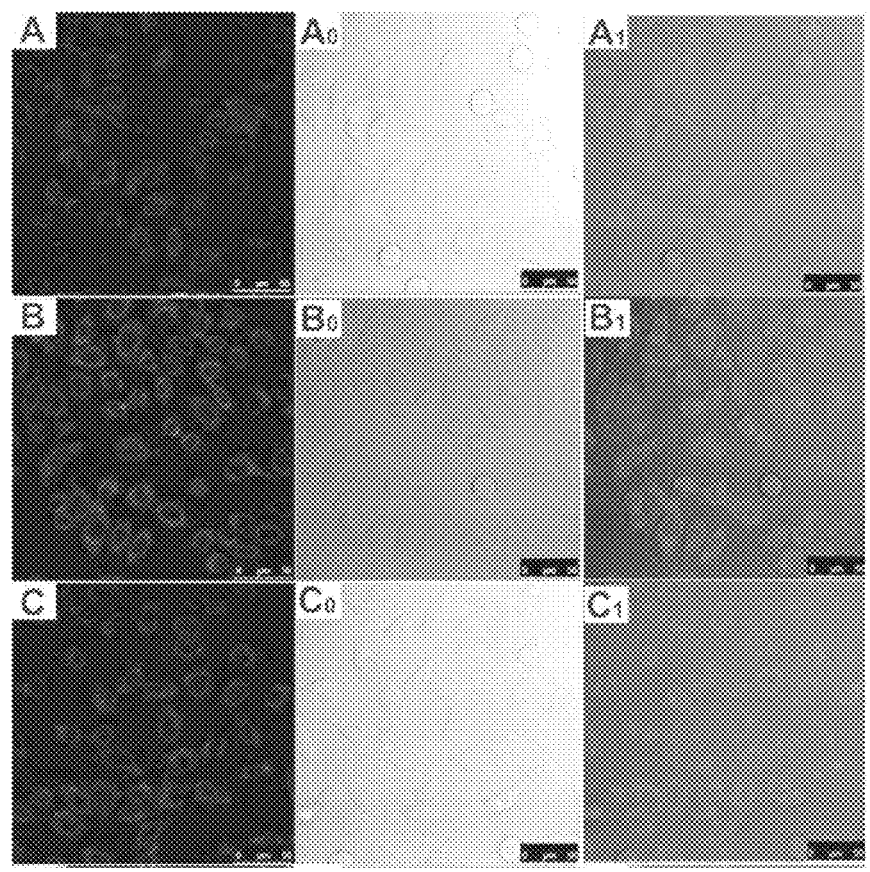
FIG. 13 shows multi-photon con-focal fluorescent microscopy image of human cervical HeLa cells after 12 hrs of exposure to the surface modified $NaYF_4:Yb^{3+}/Er^{3+}$ particles as embodied in the present invention.
Figure 14:
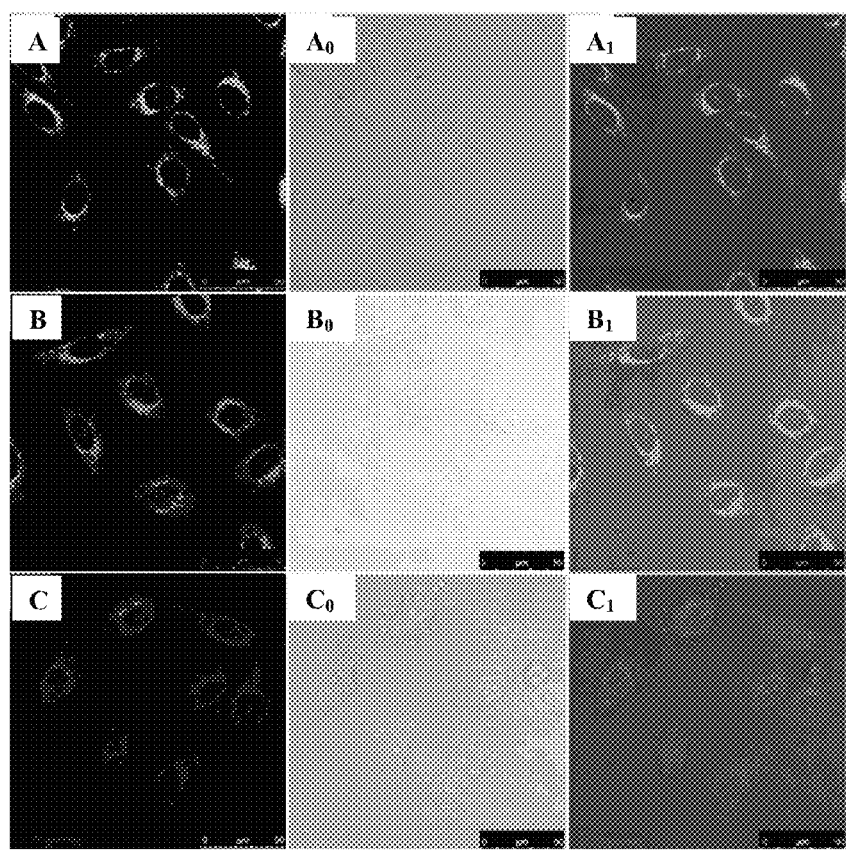
FIG. 14 shows multi-photon con-focal fluorescent microscopy image of human lung carcinoma A549 cells after 90 min of exposure to the surface modified $NaYF_4:Yb^{3+}/Er^{3+}$ particles as embodied in the present invention.
Figure 15:
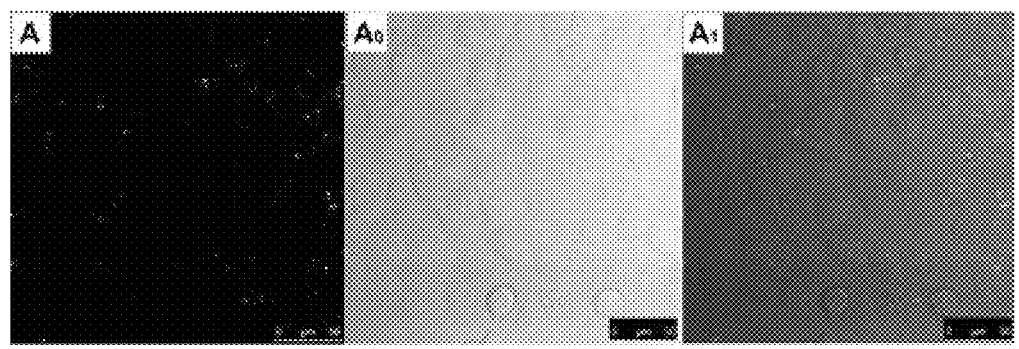
FIG. 15A shows multi-photon con-focal fluorescent microscopy image of human cervical HeLa cells after 12 hrs of exposure to the $NaYF_4:Yb^{3+}/Er^{3+}$ particles without surface modification. FIG. $15A_o$ shows the corresponding bright field images of HeLa cells. FIG. $15A_1$ shows the overlay of the corresponding fluorescent microscopy images and bright field images.

Internalization of the bare and functionalized NaYF$_4$:Yb$^{3+}$/Er$^{3+}$ particles, up-converted emissions in human lung carcinoma A549 and human cervical carcinoma HeLa cells were studied at a particle loading of 10 μg mL$^{-1}$ over an exposure period from 30 min to 24 hrs. Human lung carcinoma A549 cells were purchased from the American type Culture Collection (ATCC) (#CCL-185, ATCC, Manassas, Va., USA). Cells were cultured in Ham's F12K medium with L-glutamine and phenol red (N3520, Sigma, St. Louis, Mo., USA) supplemented with 10% fetal bovine serum at 37° C. and 5% $CO_2$. Cells were passaged every 3-5 days. Human cervical carcinoma HeLa cells were maintained in an RMPI 1640 medium supplemented with 10% fetal bovine serum (FBS) and 1% penicillin and streptomycin in 5% $CO_2$. Cells loaded with the particles modified by 3MA, 6AA and PEG were respectively excited by near-infrared (NIR) laser. To study the localization behavior of the particles, experiments were carried out in the commercial multi-photon con-focal microscopy. For the in-vitro imaging excited by NIR, the cells were imaged in the tissue culture chamber (5% $CO_2$, 37° C.) using a con-focal laser scanning microscope-Leica TCS SP5 equipped with a femtosecond-pulsed Ti: Sapphire laser (Libra II, Coherent). The excitation beam produced by the femtosecond laser, which was tunable from 680-1060 nm and focused on coverslip-adherent cells using an 43× oil immersion objective. FIG. 13 and FIG. 14 show the multi-photon con-focal fluorescent microscopy images of human cervical HeLa and human lung carcinoma A549 cells after various periods of exposure to the functionalized particles, the corresponding bright field images of HeLa cells and A549, and the overlay of the fluorescent microscopy images and bright field images. Bare and functionalized particles demonstrated very strong up-converted emission in the solution under the experimental conditions. The surface functionalized modification allows these water-soluble particles to demonstrate potential commercial value for bio-imaging. After 12 hrs of dosage time, particles functionalized by 3MA, 6AA and PEG are localized in the cytoplasm of various number of human cervical carcinoma HeLa cell lines with low toxicity for in-vitro imaging. Under excitation at about 975 nm, strong and eminent green emission ($^4S_{3/2} \rightarrow {}^4I_{15/2}$ transitions) can be observed in the cytoplasm apparent of HeLa cells, as shown in FIGS. 13A, 13B, and 13C, respectively. However, under the same experimental conditions, emission from the f-f transition of bare particles can only be observed outside the cells as shown in FIG. 15. As for the human lung carcinoma A549 cells, these three functionalized particles also demonstrated localization in the cytoplasm of various number of A549 cell lines and exhibited strong up-conversion green emission in the cytoplasm apparent of A549 cell, as shown in FIGS. 14A, B and C. A549 is a lung cancer cell line and HeLa is a cervical cancer cell line, and thus they are of different properties—epithelial lung cells in particular are known to rapidly take up particulates from their environment via endocytosis, as removal of particulate matter from the alveoli is one of their physiological functions in the body; it is likely that this property accounts for the difference in uptake rate between the cell lines.

Figure 16:
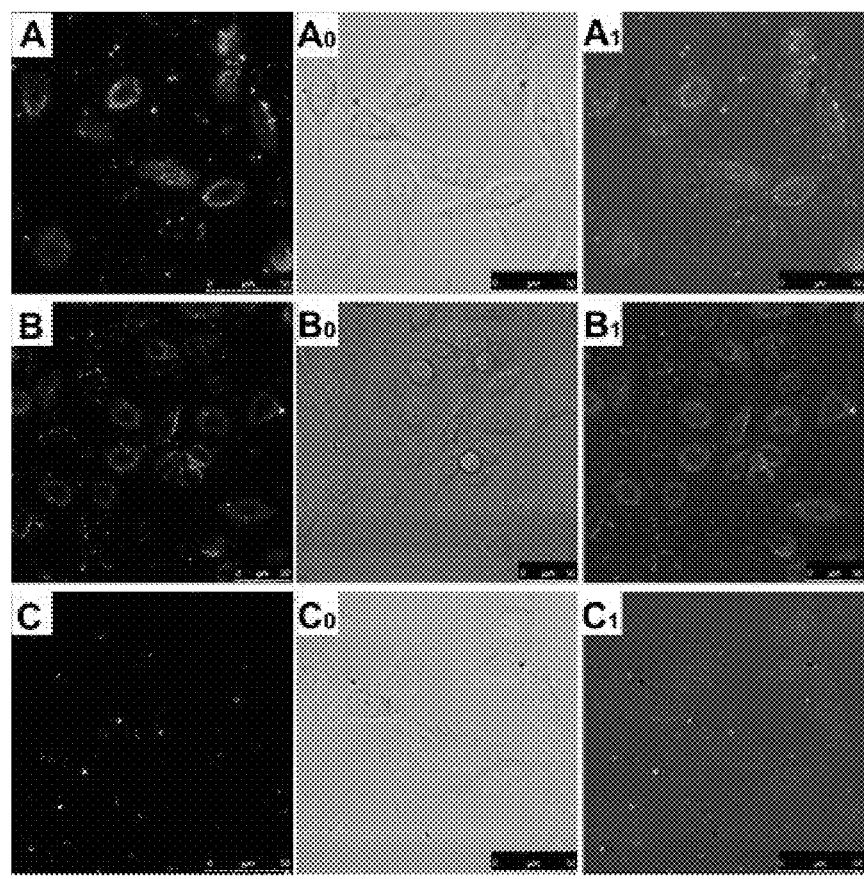
FIG. 16 shows multi-photon con-focal fluorescent microscopy image of human cervical HeLa cells after 24 hrs of exposure to the surface modified $NaYF_4:Yb^{3+}/Er^{3+}$ particles as embodied in the present invention.
Figure 17:
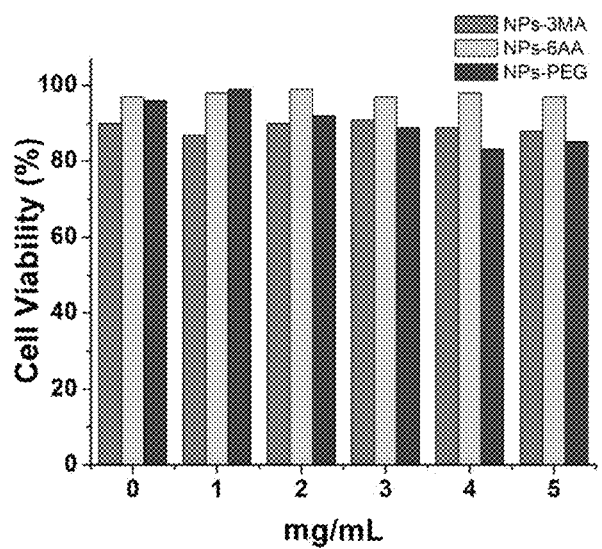
FIG. 17 shows the result from MTT assay for cytotoxicity of the 3MA, 6AA and PEG modified $NaYF_4:Yb^{3+}/Er^{3+}$ particles as embodied in the present invention.

Rather than NIR excitation, the modified $NaYF_4$: $Yb^{3+}$/$Er^{3+}$ particles can stay in the cytoplasm for more than 12 hrs with no significant cytotoxicity. In-vitro imaging of the modified particles in HeLa cells were recorded after 24 hrs dosage time and indicated that the three modified particles were remained in the cytoplasm, as shown in FIG. 16. No significant variation in the emission intensity was observed which indicated that these particles inside the cells are quite stable. Cell viability was measured using a 3-(4,5-dimethylthiazol-2-yl)-2,5 diphenyl-tetrazolium bromide (MTT) proliferation assay. Briefly, HeLa cells were seeded in a 96-well flat-bottomed microplate (6000 cells/well) and cultured in 100 µL growth medium at 37° C. and 5% $CO_2$ for 24 h. Cell culture medium in each well was then replaced by 100 µL dimethyl sulfoxide (DMSO) charged cell growth medium (max. 1:99, v/v), which contained these three particles with concentrations ranging from $10^{-7}$ to $10^{-4}$ M. After incubation for 20 hrs, 20 µL MTT labeling reagent (5 mg/mL in phosphate buffered saline solution) was added to each well for further 4 hrs incubation at 37° C. The growth medium was removed gently by suction, and 200 µL DMSO was then added to every well as solubilizing agent, sitting at room temperature overnight to dissolve the formazan crystals completely. The absorbance at the wavelength of 570 nm was measured by Multiskan EX (Thermo Electron Corporation), and each data point was represented as mean±SD from triplicate wells. FIG. 17 shows the results of the MTT assay for cytotoxicity of the 3MA, 6AA and PEG modified particles in HeLa cells. HeLa Cells were incubated separately with these three particles at 37° C. for 24 hrs. MTT assays on HeLa exposed to as much as 20 times the dose concentration of the organometallic complex for imaging for 24 hrs showed viability similar to that of the controls. This indicates that the cytotoxicity of particles as modified by 3MA, 6AA and PEG to the tested cell line was low.

Figure 18:
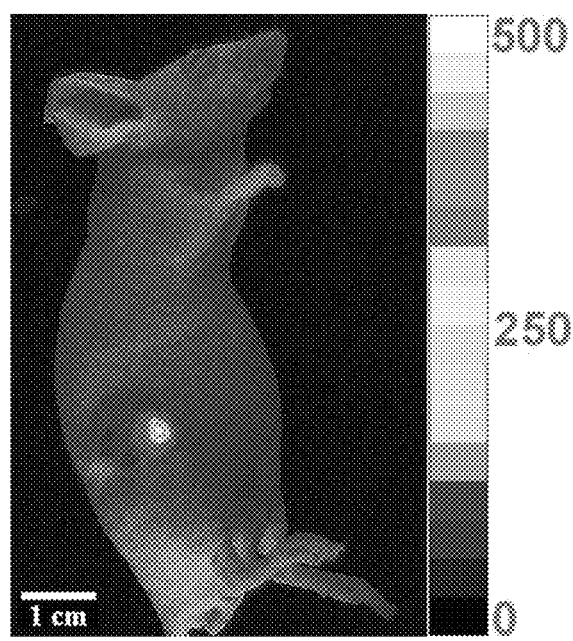
FIG. 18 shows a whole body subcutaneous imaging of the 3MA modified $NaYF_4:Yb^{3+}/Er^{3+}$ particles in a nude mouse under the excitation of 980 nm laser.

Besides of the in-vitro cell imaging of the as-prepared particles, the excitation in the NIR may not only decrease the photo damage to the biological specimens but also realize in-vivo imaging of deep tissues in animal. It has been confirmed by other studies that there was no overt toxicity for the $NaYF_4$: $Yb^{3+}$/$Tm^{3+}$ particles modified by polyacrylic acid in mice at a relatively long exposure times based on body weight data, histological, hematological and biochemical analysis. To demonstrate the feasibility of the particles in animal imaging, an aqueous solution of the surface modified $NaYF_4$: $Yb^{3+}$/$Er^{3+}$ particles was subcutaneously injected into the nude mouse and then the image was collected in our home-made system with the excitation of 980 nm laser. The injection volume is 200 µL with the concentration of 3.5 mg/mL. Fluorescent imaging is conducted in our home-made system with 980 nm diode laser. To avoid interference of the excitation light, an emission filter (850 SP) is put in front of CCD camera. Under the excitation of the 980 nm laser, emission spectrum ranges from visible light 515 to 670 nm, and NIR light of 750-808 nm are achievable. According to the emission spectra of the $NaYF_4$:$Yb^{3+}$/$Er^{3+}$ particles as synthesized, imaging between 520-540 nm using 530/20 filter was captured. The whole body subcutaneous imaging of the particles in nude mouse is shown in FIG. 18. As shown in the figure, obvious emissive spot can be seen in the subcutaneous region, which indicates that the as-prepared particles from the embodied method demonstrated potential applications in in-vivo and deep imaging of animals.

It should be understood that the above only illustrates and describes examples whereby the present invention may be carried out, and that modifications and/or alterations may be made thereto without departing from the spirit of the invention.

It should also be understood that certain features or steps of the invention, which are, for clarity, described in the context of separate embodiments, may also be provided in combination in a single embodiment. Conversely, various features or steps of the invention which are, for brevity, described in the context of a single embodiment, may also be provided or separately or in any suitable subcombination.

What is claimed is:

1. A method of synthesizing water-soluble particles, the method comprising:
    providing a solution comprising a halide compound, a first solvent, and a mixture of $YCl_3$, $YbCl_3$, and $ErCl_3$, wherein the YbCl$_3$ and total amount of the YCl$_3$, YbCl$_3$, and ErCl$_2$ are in a mole ratio in the solution ranging from about 12% to about 20%, and the ErCl$_3$ and the total amount of the YCl$_3$, YbCl$_3$ and ErCl$_3$ are in a mole ratio in the solution ranging from about 1% to about 5%;

introducing a capping agent, selected from the group consisting of 3-mercaptopropionic acid, 6-aminocaproic acid, and mixtures thereof, into the solution to form a mixture;

heating the mixture under pressure to produce a plurality of particles; and recovering the particles from the mixture.

2. The method of claim 1, wherein the first solvent is selected from the group consisting of ethylene glycol, water, and mixtures of ethylene glycol and water.

3. The method of claim 1, wherein the halide compound is selected from the group consisting of chlorides, fluorides, and mixtures of chlorides and fluorides.

4. The method of claim 3, wherein the chloride is NaCl.

5. The method of claim 3, wherein the chloride is in a concentration ranging from about 0.025 mmol per ml to about 0.1 mmol per ml.

6. The method of claim 3, wherein the fluoride is selected from the group consisting of NaF, NH$_4$F, NH$_4$HF$_2$, and mixtures thereof.

7. The method of claim 3, wherein the fluoride is in a concentration ranging from about 0.25 mmol per ml to about 1.0 mmol per ml.

8. The method of claim 1, further comprising stirring the solution.

9. The method of claim 8, wherein the stirring comprises stirring for about 20 min to 60 min.

10. The method of claim 1, wherein the heating comprises heating at a temperature ranging from about 120° C. to about 220° C.

11. The method of claim 1, wherein the heating comprises heating for about 4 hrs to about 48 hrs.

12. The method of claim 1, wherein the heating comprises heating under a pressure ranging from about 1.5 MPa to about 2.5 MPa.

13. The method of claim 1, wherein the heating comprises heating in an autoclave.

14. The method of claim 1, further comprising cooling after the heating.

15. The method of claim 14, including cooling by natural cooling.

16. The method of claim 1, wherein the recovering comprises separating the particles via centrifugation, and collecting the particles.

17. The method of claim 1, further comprising washing the particles recovered with a second solvent to produce washed particles.

18. The method of claim 17, wherein the second solvent comprises ethanol.

19. The method of claim 17, wherein the washing is repeated from 2 times to 5 times.

20. The method of claim 17, further comprising drying in which the washed particles are dried in vacuum at a temperature ranging from about 45 to about 70° C. for about 12 hrs to about 24 hrs.

21. The method of claim 1, wherein the halide compound is NaF and the particles are NaYF$_4$:Yb$^{3+}$/Er$^{3+}$.

22. The method of claim 1, wherein the particles comprise at least one surface functional group selected from the group consisting of —COOH, —NH$_2$, —SH, —OH, and mixtures thereof.

23. The method of claim 1, comprising dissolving the mixture of YCl$_3$, YbCl$_3$, and ErCl$_3$ in the first solvent to form a first solution, and separately dissolving the halide compound in a second solvent to form a second solution, followed by combining the first and second solutions to form the solution.

24. The method of claim 23, wherein the first solvent comprises ethylene glycol.

25. The method of claim 23, wherein the second solvent comprises water.

* * * * *